United States Patent [19]

Kobayashi et al.

[11] Patent Number: 5,869,440
[45] Date of Patent: Feb. 9, 1999

[54] PEROXIDE ACTIVATION METHOD AND PEROXIDE COMPOSITION

[75] Inventors: Tsuneo Kobayashi, Ninomiya; Masahito Mikami, Hadano; Shuzo Nakamura, Minoo, all of Japan

[73] Assignee: S. C. Johnson & Son, Inc., Racine, Wis.

[21] Appl. No.: 793,533

[22] PCT Filed: Aug. 30, 1995

[86] PCT No.: PCT/JP95/01718

§ 371 Date: May 12, 1997

§ 102(e) Date: May 12, 1997

[87] PCT Pub. No.: WO96/06912

PCT Pub. Date: Mar. 7, 1996

[30] Foreign Application Priority Data

Aug. 31, 1994 [JP] Japan .................................. 6-241757
Dec. 22, 1994 [JP] Japan .................................. 6-340807

[51] Int. Cl.$^6$ ............................. C11D 3/08; C11D 3/395; C11D 7/18; C11D 7/54
[52] U.S. Cl. ......................... 510/372; 510/376; 510/501; 252/186.41; 8/111
[58] Field of Search .................................. 510/367, 372, 510/375, 6; 252/186.41; 8/111

[56] References Cited

U.S. PATENT DOCUMENTS

| | | | |
|---|---|---|---|
| 2,927,840 | 3/1960 | Dithmar et al. ............................. | 8/111 |
| 3,345,303 | 10/1967 | Schmid et al. ........................... | 252/186 |
| 3,756,774 | 9/1973 | Kirner .......................................... | 8/111 |
| 4,023,453 | 5/1977 | Kravetz et al. ........................... | 252/102 |
| 4,086,175 | 4/1978 | Kravetz et al. ............................. | 252/99 |
| 4,086,177 | 4/1978 | Kubitschek et al. ..................... | 252/102 |
| 5,620,563 | 4/1997 | Chen ......................................... | 162/65 |

FOREIGN PATENT DOCUMENTS

| | | |
|---|---|---|
| 8475 A1 | 5/1980 | European Pat. Off. . |
| 35 19 689 | 4/1986 | Germany . |

*Primary Examiner*—Paul Lieberman
*Assistant Examiner*—John M Petruncio
*Attorney, Agent, or Firm*—Laura L. Bozek

[57] ABSTRACT

Provided herein is a method of peroxide activation which comprises combining (1) an aqueous bleaching solution with hydrogen peroxide base, and (2) an aqueous solution containing as major components a sufficient amount of dicyandiamide for hydrogen peroxide activation, and an organic builder and/or inorganic builder, and maintaining the combined solution at alkaline pH. These solutions are stable when stored in separate containers. As needed, the solutions are mixed together. This invention is effective for bleaching soil and for removing mold, applicable for cleaning, bleaching, sterilizing or deodorizing in either domestic or industrial use.

7 Claims, No Drawings

PEROXIDE ACTIVATION METHOD AND PEROXIDE COMPOSITION

DETAILED EXPLANATION OF THE INVENTION

1. Technical Field

This invention relates to a bleaching agent chiefly containing hydrogen peroxide and which is suitable for both domestic and industrial use. In detail, this invention relates to a bleaching agent having strong bleaching power and which is effective for cleaning, bleach-sterilizing and deodorizing, especially for mold-removal.

2. Background Art

Chlorine bleaches containing sodium hypochlorite have been conventionally used to remove mold. However, the strong odor of hypochlorite causes users discomfort when they use chlorine bleaches. In addition, toxic chlorine gas is generated when a chlorine bleach is mixed with an acidic detergent. On the other hand, hydrogen peroxide has no strong odor, and no chlorine gas is generated when hydrogen peroxide is mixed with an acidic detergent. Bleaches containing hydrogen peroxide are suitable for removing mold, but much weaker in bleaching power than the above-mentioned chlorine bleaches. Thus conventional bleaches containing hydrogen peroxide cannot satisfy consumer demands.

In order to improve the bleaching power of hydrogen peroxide, various methods have been tried to accelerate the decomposition of hydrogen peroxide.

Japanese Kokoku Patent No. Sho 60[1985]-18720 describes the use of both cyanamide and a Group IIA metal compound for activation of peroxide, Japanese Kokai Patent Application No. Sho 63[1988]-161089 describes the use of both cyanamide and hydroxycarboxylic acid as activators. Japanese Kokai Patent Application No. Sho 63[19881]-161090 describes the use of both cyanamid and a chelating agent such as EDTA as activators. Japanese Kokai Patent Application No. Sho 62[1987]-72789 discloses the use of acrylonitrile polymer, and Japanese Kokai Patent Application No. Sho 52[19771]-52880 describes the use of a nitrile compound of A-CO—CN {A=OR, —N(R)$_2$} as an activator. Japanese Kokai Patent Application No. Sho 62[19871]-149800 describes the use of nitriles such as phthalonitrile, isophthalonitrile or cyanates as activators. Japanese Kokai-Patent Application No. Hei 1[19891]-190797 describes the use of acrylonitrile polymer as an activator. Japanese Kokai Patent Application Nos. Sho 64[1989]-45499, Sho 64[1989]-68347 and Sho 64[1989]-69697 and Hei 4[1992]-253947 describe the use of a nitrile compound containing a cationic group in the molecule as an activator.

The above-mentioned activators are used in a form of an aqueous solution, and they are mixed with peroxide at the point of bleaching to accelerate the decomposition of the peroxide. The aqueous solutions of activating agents are generally unstable, and in the two aqueous component system like the present invention, the activity is lost during storage and the bleach becomes no longer effective before use.

This invention has overcome the poor storage stability of the conventional products and provides an activation method for accelerating peroxide solution decomposition in alkali.

SUMMARY DISCLOSURE OF THE INVENTION

The object of the present invention is to provide an activation method to accelerate the peroxide decomposition using an alkaline solution with improved storage stability.

The inventors investigated the above-mentioned problems with the intent to solve them. In Japanese Kokai Patent Application No. Sho 52[1977]-110287, a system using dicyandiamide and an aqueous sodium hydroxide solution is disclosed as a comparative example with unsatisfactory bleaching effects. The inventors investigated the peroxide-decomposing mechanism of dicyandiamide, then completed this invention.

This invention involves an activation method for a hydrogen peroxide bleach of two aqueous solutions, in which two solutions, that is, (1) a bleaching aqueous solution with hydrogen peroxide base, and (2) an aqueous solution chiefly containing a suitable amount of dicyandiamide for hydrogen peroxide activation and an organic builder and/or an inorganic builder are mixed and kept alkaline. Further, the present invention provides a bleaching composition comprising (1) a bleaching aqueous solution with hydrogen peroxide base, and (2) an aqueous solution chiefly containing a suitable amount of dicyandiamide for hydrogen peroxide activation and an organic builder and/or an inorganic builder.

BEST MODE FOR CARRYING OUT THE INVENTION

Conventional hydrogen peroxide solutions having concentrations of 0.1 to 90 wt %, preferably 0.5 to 35 wt %, can be used for the aqueous bleaching solution with hydrogen peroxide base. Solutions of hydrogen peroxide of various concentrations (from 3.0 to 60 wt %) are commercially available, but those higher than 6% are classified into the powerful drugs other than medicine under Japanese Regulation Law on toxicants and powerful drugs. Therefore, for domestic or industrial use, it is preferable to use hydrogen-peroxide of concentrations not higher than 6% in order not to be designated to the powerful drug. To stabilize the hydrogen peroxide solution, the pH of the solution is adjusted not higher than 9.0. Organic acids such as lactic acid, inorganic acids such as phosphoric acid, organic phosphate esters such as phytic acid, alkali agents such as sodium hydroxide, potassium hydroxide and sodium carbonate, EDTA metal salts, can be used phosphate salts, and silicate salts. If necessary, any conventional stabilizers can be used.

As a stabilizer for hydrogen peroxide, there are EDTP (ethylene diamine tetramethylene phosphonic acid), sodium stannate, phytic acid, 1-hydroxyethane-1,1-diphosphonic acid, preferably propanediaminetetramethylene phosphonic acid (PDTP). Depending on the concentration of hydrogen peroxide and pH, the concentration of the added stabilizer is in the range of 0.001 to 4 wt %.

Dicyandiamide, an activator for hydrogen peroxide, exerts no effect when used alone. It is used in a system containing an organic or inorganic builder. The organic builder of low molecular weight includes aminocarboxylic acid builder such as EDTA alkali metal salts, EDTA di(alkali metal)(alkaline-earth metal) salts, nitriloacetate alkali metal salts, DTPA alkali metal salts and HEDTA alkali metal salts; oxycarboxylic acid builder such as citric acid alkali metal salts, carboxymethyloxysuccinate, gluconic acid alkali metal salts, glycolic acid alkali metal salts; and phosphonic acid builder such as 1-hydroxyethane-1,1-diphosphate alkali metal salts and 2-phosphonobutanetricarboxylate 1, 2, 4-alkali metal salts. The organic builder of high molecular weight includes acrylate vinylsulfonate, acrylate-vinylalcohol polymer, acrylate-methylvinylether copolymer, 2-hydroxyacrylate-acrylate copolymer, and maleate-vinylalcohol copolymer. The inorganic builder includes phosphate builder such as tripolyphosphate, pyrophosphate, phosphate, metaphosphate and hexametaphosphate; silicate builder such as metasilicate, orthosilicate, sodium silicate, potassium silicate, lithium silicate, barium silicate, magnesium silicate and ammonium silicate; borate builder such as borate and borax; carbonate builder and sulfonate, among which silicate is preferable. Along with the above-mentioned organic builder or inorganic builder, an alkali agent such as sodium hydroxide and potassium hydroxide can be added. It is impossible to maintain the excellent peroxide-activating ability for a long time when only the alkali agent without the builder is contained.

In the present invention, the mixture of (1) an aqueous bleaching solution with hydrogen peroxide base (herein after referred Solution A) and (2) an aqueous solution mainly containing sufficient amount of dicyandiamide to activate hydrogen peroxide and organic builder/inorganic builder (herein after referred Solution B), is maintained at alkaline pH to make hydrogen peroxide decompose, so as to be used as an agent for cleaning, bleaching, sterilizing, deodorizing etc. in domestic or industrial use.

Solutions A and B can be mixed in an arbitrary ratio, but usually in a ratio of 1:10 to 10:1. The amount of hydrogen peroxide in Solution A is determined so that the final concentration after mixing becomes 0.3 to 30 wt %, preferably 0.5 to 6.0 wt %. If the concentration is lower than 0.3 wt %, the bleaching effect is not sufficient. If the hydrogen peroxide concentration is higher than 6.0 wt %, it comes under "powerful drug not for medical use" under the Japanese regulation law for toxicants and powerful drugs, and it may cause problematically irritation to the skin and eyes. The molar ratio of dicyandiamide to hydrogen peroxide to activate hydrogen peroxide is preferably in a range of 0.1 to 10. The dicyandiamide concentration in Solution B is determined from the use ratio of Solutions A and B and the use amount of hydrogen peroxide. Usually, it is 2 to 20 wt % of Solution B. If the dicyandiamide concentration is lower than 0.1 in molar ratio to hydrogen peroxide, the activation effect is small, and the use of more than 10 mole can not increase the effect further. The amount of the builder to be used is determined to be in a range of 0.05 to 10.0 wt % in the mixture. The builder is used to increase the hydrogen peroxide-activation effect of dicyandiamide and it has no effect in the concentration lower than 0.05 wt %, and excess concentration higher than 10 wt % cannot increase the effect further.

Solution A containing hydrogen peroxide and Solution B containing dicyandiamide and a builder are mixed for bleaching, where pH of the mixture should be kept in an alkaline range of 8.0 to 13.0. If pH is lower than 8.0, the benefit of the present invention cannot be achieved and strong alkaline condition such as more than pH 13, is unnecessary. When the amounts of hydrogen peroxide, dicyandiamide and the builder are in the above ranges, conventional alkaline agents such as sodium hydroxide and potassium hydroxide can be added to control pH. Further, conventional detergent components such as surfactant, hydrotropic agent, solvent, and thickener can be added in an arbitrary amount.

As the surfactant, anionic surfactants and nonionic surfactants are preferable. Anionic surfactants include anionic surfactants of sulfuric ester salt type such as higher alcohol sulfuric ester salt, higher alkylether sulfuric ester salt, sulfated oil, sulfated fatty acid ester and sulfated olefin; sulfonate type anionic surfactants such as alkylbenzene sulfonate, alkylnaphthalene sulfonate, paraffin sulfonate, α-olefin sulfonate, N-methyl-N-oleyltaurine, and sulfosuccinic diester salt; anionic surfactants of phosphoric ester salt type such as alkyl phosphate and polyoxyethylene alkylether phosphate; organic fatty acid salts exemplified with palm oil fatty acid and sodium sarcosine.

More preferable examples of anionic surfactants include sulfonates containing alkyl or alkylphenyl groups with carbon number of 8 to 22, sulfuric ester salts, and sulfuric esters containing either alkyl alcohols or alkylphenols with carbon numbers of 8 to 22 to which either ethylene oxide (EO) or propylene oxide (PO) is attached. In this case, 1 to 6 mol of EO or PO is preferable.

Nonionic surfactants include polyethylene glycol-type nonionic surfactants such as an ethylene oxide adduct of higher alcohol, ethylene oxide adduct of alkyl phenol, ethylene oxide adduct of fatty acid, ethylene oxide adduct of polyhydric alcohol-fatty acid ester, ethylene oxide adduct of higher alkylamine, ethylene oxide adduct of fatty acid amide, ethylene oxide adduct of oil, ethylene oxide adduct of propylene glycol; polyhydric alcohol-type nonionic surfactant exemplified with fatty acid ester of glycerol, fatty acid ester of pentaerythritol, fatty acid ester of sorbitol and sorbitan, fatty acid ester of sucrose, polyhydric alcohol alkylether, fatty acid alkanol amide and alkylamine oxide. Preferable examples of nonionic surfactants include alcohols or phenols having an alkyl group or an alkylphenyl group with carbon numbers of 8 to 22 to which 5 to 20 mol of ethylene oxide (EO) or propylene oxide (PO) is added. Amine oxide are also included. An N-alkyl-N,N-dimethylamine oxide of which alkyl group has carbon number of 8 to 20 can be used. In particular, N-lauryl-N,N-dimethylamine oxide is preferred. Cyclic amine oxides such as N-methylmorpholino amine oxide or N-methylpiperidinoamine oxide can also be used.

Dicyandiamide, the activating agent, has low solubility in water and when a solution of high concentration is prepared, it will problematically precipitate due to supersaturation when it is left standing at low temperature. In order to stabilize the solution at either low or high temperatures, 0 to 20%, preferably 1 to 10%, of a hydrotropic agent is added. Examples of such a hydrotropic agent include alcohols and polyhydric alcohols such as ethanol, tertiary butanol, Solufit (2-methyl-3-methoxybutyl alcohol), ethylene glycol, diethylene glycol, propylene glycol, dipropylene glycol, hexylene glycol, isopropylene glycol and glycerin; derivatives of polyhydric alcohols such as alkylene glycol ethers which are mono- and di-alkyl (methyl, ethyl, propyl, butyl, phenyl, hexyl, etc.) ester thereof including Carbitol, butylcarbitol, ethylene glycol monobutylether, cellosolve, ethylcellosolve, etc.; alkylbenzene sulfonates such as toluene sulfonate, xylene sulfonate and butylmetaxylene sulfonate; and generally used detergent additives such as urea. These additives are added in an amount of 0 to 60 wt %, preferably 1 to 40 wt %.

The viscosity of the composition is increased by adding a viscosity improver to Solution A and/or Solution B, so that when the mixed agent is applied to a ceiling surface, a vertical surface or an inclined surface, the drip of the mixed solution from the surface may become minimum. Examples of viscosity improver include synthetic or semi-synthetic polymers such as acrylic polymers or cellulose derivatives, natural polymers such as xanthan gum, bee gum, and inorganic viscosity improvers such as alumina sol.

Following Examples and Comparative Examples are provided to explain the present invention concretely without limiting the scope of the invention.

1. Methods to Test and Evaluate Mold Bleaching a) Mold Culture

Aureobasidum pullulans was inoculated on an autoclaved agar medium in a sterilized petri dish, and cultured for 30 days at 35° C. in the incubator.

b) Mold Bleaching Test

A glass tube of given length was vertically inserted into the agar medium where Aureobasidium pullulans has grown.

Then the glass tube was filled with a mixed bleach composition and left for 1 hour. The bleaching degree of *Aureobasidium pullulans* was evaluated.

c) Evaluation

Lightness (L value) of the mold-grown agar medium was measured using a color-difference meter (CS-100, Minolta) and a data processor (DP-101, Minolta) before and after the above-mentioned bleaching. Bleaching rate (%) is calculated using the following equation.

Bleaching rate (%)={(L value after bleaching)−(L value before bleaching)}/{(L value of agar medium)−(L value before bleaching)}×100

2. Bleaching Test for Tea-stained Cloth a) Preparation of Black Tea-stained Cloth Commercially available black tea leaves (20 g) were added into 1 liter of boiling water and simmered for 5 minutes. The tea leaves were removed and 5 pieces of broadcloth (30×30 cm, starch-free) were soaked in the brewed tea and cooked for 30 minutes. Then the cloth was taken out and dried. Each dried cloth was cut into 10×10 cm pieces for the bleaching test.

b) Bleaching Test

The bleaching composition (20 g) was put into a beaker, into which a piece of the tea-stained cloth was soaked for 5 minutes. Then the cloth was taken out, rinsed well with tap water and dried. The reflectivity of the dried cloth was measured with a color difference meter (made by Tokyo Denshoku K. K., model TC-1500). The bleaching rate (%) was obtained by the following equation:

Bleaching rate (%){(Reflectivity after bleaching)−(Reflectivity before bleaching)}/{(Reflectivity of unstained cloth)−(Reflectivity before bleaching)}×100.

EXAMPLES 1–10 AND COMPARATIVE EXAMPLES 1 AND 2

A hydrogen peroxide solution (5.5 wt %) (Solution A) in a container A and a solation containing 7.0 wt % dicyandiamide and a builder in an amount as listed in Table 1 (Solution B) In a container B were mixed at 1:1. The mixture was poured onto the mold on the agar medium to compare the bleaching effect.

As shown in Table 1, any combination of hydrogen peroxide, dicyandiamide and the builder was excellent in mold-bleaching effect. To the contrary, any comparative combination not containing dicyandiamide or the builder had little mold bleaching effect.

TABLE 1

|  | Example |  |  |  |  |  |
|---|---|---|---|---|---|---|
| Composition | 1 | 2 | 3 | 4 | 5 | 6 |
| Solution A |  |  |  |  |  |  |
| Hydrogen Peroxide (%) IE water | 5.5 | 5.5 | 5.5 | 5.5 | 5.5 | 5.5 |
|  |  |  | remainder |  |  |  |
| Total Solution A | 100 | 100 | 100 | 100 | 100 | 100 |
| Solution B |  |  |  |  |  |  |
| Dicyandiamide | 4.0 | 7.0 | 7.0 | 7.0 | 7.0 | 7.0 |
| Na orthosilicate | 3.0 | 3.0 | 6.0 |  |  |  |
| Na metasilicate |  |  |  | 2.8 |  |  |
| No. 3 Na silicate |  |  |  |  |  |  |
| Sodium carbonate |  |  |  |  |  | 2.8 |

TABLE 1-continued

| EDTA-4Na |  |  |  |  | 2.8 |  |
| EDTA-2Na Mg |  |  |  |  |  |  |
| NTA-3Na |  |  |  |  |  |  |
| K pyrophosphate |  |  |  |  |  |  |
| IE water |  |  | remainder |  |  |  |
| Total Solution B | 100 | 100 | 100 | 100 | 100 | 100 |
| pH of mixed solution (A:B = 1:1) | 10.8 | 10.8 | 11.1 | 10.6 | 12.5* | 10.8* |
| Bleaching rate (%) | 34.4 | 79.9 | 69.2 | 76.4 | 20.1 | 35.1 |

|  | Example |  |  |  | Comp. Exmp |  |
|---|---|---|---|---|---|---|
| Composition | 7 | 8 | 9 | 10 | 1 | 2 |
| Solution A |  |  |  |  |  |  |
| Hydrogen Peroxide | 5.5 | 5.5 | 5.5 | 5.5 | 5.5 | 5.5 |
| (%) in IE water |  |  |  |  |  |  |
| Total Solution A | 100 | 100 | 100 | 100 | 100 | 100 |
| Solution B |  |  |  |  |  |  |
| Dicyandiamide | 7.0 | 7.0 | 7.0 | 7.0 |  | 7.0 |
| Na orthosilicate |  |  |  |  | 3.0 |  |
| Na metasilicate |  |  |  |  |  |  |
| No. 3 Na silicate |  |  |  |  | 3.0 |  |
| Sodium carbonate |  |  |  |  |  |  |
| EDTA-4Na |  |  |  |  |  |  |
| EDTA-2Na Mg | 2.8 |  |  |  |  |  |
| NTA-3Na |  | 2.8 |  |  |  |  |
| K pyrophosphate |  |  | 2.8 |  |  |  |
| IE water |  |  | remainder |  |  |  |
| Total Solution B | 100 | 100 | 100 | 100 | 100 | 100 |
| pH of mixed solution (A:B = 1:1) | 10.8 | 10.6 | 10.7 | 10.5 | 10.9 | 5.1 |
| Bleaching rate (%) | 26.0 | 10.9 | 17.9 | 76.8 | 1.6 | 0.0 |

*: Trace of NaOH is added to control the pH of the mixture.
IE water: Ion Exchanged Water

EXAMPLE 11 AND COMPARATIVE EXAMPLES 3 AND 4

Solution A (5.5 wt % hydrogen peroxide) in the container A and Solution B (4.0 wt % of dicyandiamide, 3.0 wt % of sodium orthosilicate) in the container B were incubated at 50° C. in an incubator for 5 days. After that, they were mixed at 1:1 and the mixture was poured onto the mold grown on the agar medium to observe the bleaching effect. In Comparative Example 3, sodium orthosilicate, the inorganic builder, was replaced with sodium hydroxide, an alkali agent. In the Comparative Example 4, a known activator triacetin was used in place of dicyandiamide.

In Example 11, the bleaching rate is good both immediately after preparation and after 5 days incubation in comparison with Comparative Example. The storage stability of the bleaching agent of invention is clearly better than that of Comparative Example.

TABLE 2

|  | Example | Comp. Example |  |
|---|---|---|---|
| Composition | 10 | 3 | 4 |
| Solution A |  |  |  |
| $H_2O_2$ (%) | 5.5 | 5.5 | 5.5 |
| IE water | remainder | remainder |  |
| Total of Solution A | 100 | 100 | 100 |

TABLE 2-continued

| Composition | Example 10 | Comp. Example 3 | Comp. Example 4 |
|---|---|---|---|
| Solution B | | | |
| Dicyandiamide | 4.0 | 4.0 | |
| Triacetin | | | 4.0 |
| Na Orthosilicate | 3.0 | | 3.0 |
| Sodium Hydroxide | | 3.0 | |
| IE water | remainder | remainder | |
| Total of Solution B | 100 | 100 | 100 |
| pH of Mixed solution A:B = 1:1 | 10.8 | 10.8 | 10.9 |
| Bleaching rate (%) immediately after preparation | 34.4 | 32.2 | 22.0 |
| Bleaching rate (%) after 5 days at 50° C. incubation | 25.8 | 19.3 | 4.4 |
| (% reduction of bleaching rate) | (25%) | (60%) | (80%) |

EXAMPLE 12 AND COMPARATIVE EXAMPLES 5 AND 6

A hydrogen peroxide solution (5.5 wt %) in Container A and a solution of dicyandiamide (7.0 wt %) and sodium orthosilicate (3.0 wt %) in Container B were mixed at a ratio of 1:1. The tea-stained cloth was soaked in the mixed solution, then washed with water and dried. The result in Table 3 clearly shows that the combination of Example, hydrogen peroxide, dicyandiamide and the builder, was effective for bleaching the tea-stained cloth. On the other hand, in Comparative Examples not containing one of dicyandiamide and the builder, the bleaching effect is clearly weak. The combination of hydrogen peroxide, dicyandiamide and the builder is more effective for bleaching the tea-stained cloth.

TABLE 3

| Composition | Example 12 | Comp. Example 6 | Comp. Example 6 |
|---|---|---|---|
| Solution A | | | |
| H$_2$O$_2$ (%) | 5.5 | 5.5 | 5.5 |
| IE water | remainder | remainder | |
| Total of Solution A | 100 | 100 | 100 |
| Solution B | | | |
| Dicyandiamide | 7.0 | | 7.0 |
| Na Orthosilicate | 3.0 | 3.0 | |
| IE water | remainder | remainder | |
| Total of Solution B | 100 | 100 | 100 |
| pH of A:B (1:1) Mixture | 11.2 | 11.2 | 7.3 |
| Bleaching rate (%) | 100 | 64.6 | 5.5 |

EXAMPLE 13 AND COMPARATIVE EXAMPLE 7

The Solution A (5.5 wt % hydrogen peroxide) in the container A and the Solution B (4.0 wt % of dicyandiamide, 3.0 wt % of sodium orthosilicate) in the container B were incubated at 50° C. in an incubator for 30 days. After that, they were mixed at 1:1. Into the mixture, a piece of tea-stained cloth was soaked for 5 minutes then washed and dried to estimate bleaching effect. In Comparative Example 7, instead of sodium orthosilicate as an inorganic builder, the alkali agent, sodium hydroxide was used.

In Example 13, the bleaching rate after incubation at 50° C., 30 days is clearly better in comparison with Comparative Example.

TABLE 4

| Solution Composition | Example 13 | Comp. Example 7 |
|---|---|---|
| Solution A | | |
| H$_2$O$_2$ (%) | 6.0 | 6.0 |
| IE water | remainder | remainder |
| Total of Solution A (%) | 100 | 100 |
| Solution B | | |
| dicyandiamide | 4.0 | 4.0 |
| Na Orthosilicate | 3.0 | |
| Sodium hydroxide | | 3.0 |
| IE water | remainder | remainder |
| Total of Solution B (%) | 100 | 100 |
| pH of Mixture A:B (1:1) | 10.8 | 11.6 |
| Bleaching rate (%) immediately after preparation | 100 | 100 |
| Bleaching rate (%) after 30° C., 50 days incubation | 100% | 65% |

INDUSTRIAL APPLICABILITY

When a bleaching aqueous solution with hydrogen peroxide base and an aqueous solution of alkaline dicyandiamide are stored in separate containers as in this invention, the solutions can be stable over a long period of time. When needed, the solutions are mixed together, and the mixture of this invention is effective for bleaching soil and for removing mold, applicable for cleaning, bleaching, sterilizing or deodorizing in either domestic or industrial use.

We claim:

1. A method for peroxide activation of a hydrogen peroxide bleaching agent composed of two aqueous solutions, comprising:

combining (1) an aqueous bleaching solution with hydrogen peroxide base, and (2) an aqueous solution containing as components an amount of dicyandiamide effective for hydrogen peroxide activation, and an organic builder and/or inorganic builder, and maintaining the combined solution at alkaline pH of at least 8.0;

wherein solution (1) and solution (2) are stable for at least 30 days at 50° C.; the molar ratio of dicyandiamide to hydrogen peroxide for hydrogen peroxide activation is in a range of 0.1 to 10: wherein the solutions are combined in a ratio of 1:10 to 10:1; the combined solution has a builder concentration of 0.05% to 10% by weight; and wherein the builder is selected from the group consisting of metal salts of ethylenediaminetetraacetic acid, dialkali metal salts of ethylene diaminetetraacetate, alkali earth metal salts, metal salts of nitriloacetate, citrates, carboxymethyoxysuccinates, tripolyphosphates, silicates, borates, carbonates, sulfonates and sulfates.

2. The method of peroxide activation as claimed in claim 1, wherein the aqueous bleaching solution (1) is an acidic solution.

3. The method of peroxide activation as claimed in claim 1, wherein the pH of the combined solution is 8.0 to 13.0.

4. The method of peroxide activation as claimed in claim 1, wherein the pH of the combined solution is 9.0 to 11.0.

5. The method of peroxide activation as claimed in claim 1, wherein (1) an aqueous bleaching solution containing hydrogen peroxide and (2) an aqueous solution containing a suitable amount of dicyandiamide for hydrogen peroxide activation and an organic builder and/or inorganic builder, are stored in separate containers, and combined in a predetermined ratio at need to use.

6. The method of peroxide activation as claimed in claim 1, wherein the inorganic builder is a silicate selected from the group consisting of sodium silicate, potassium silicate, lithium silicate, barium silicate, magnesium silicate and ammonium silicate.

7. A bleaching kit, comprising (1) a first aqueous bleaching solution with hydrogen peroxide base, and (2) a second aqueous solution containing as components an amount of dicyandiamide effective for hydrogen peroxide activation, and organic builder and/or inorganic builder;

wherein the first and second solutions are stable for at least 30 days at 50° C.; the molar ratio of dicyandiamide to hydrogen peroxide for hydrogen peroxide activation is in a range of 0.1 to 10; wherein the first and second solutions are combined in a ratio of 1:10 to 10:1 to form a combined aqueous solution, the combined aqueous solution having a pH of at least 8.0, a builder concentration of 0.05 to 10 percent by weight; and wherein the builder is selected from the group consisting of metal salts of ethylenediaminetetraacetic acid, dialkali metal salts of ethylene diaminetetraacetate, alkali earth metal salts, metal salts of nitriloacetate, citrates, carboxymethyoxysuccinates, tripolyphosphates, silicates, borates, carbonates, sulfonates and sulfates.

\* \* \* \* \*